United States Patent [19]

Ilgner et al.

[11] Patent Number: 4,528,147
[45] Date of Patent: Jul. 9, 1985

[54] PROCESS FOR HUMIDIFYING A GAS STREAM, PARTICULARLY IN METHANOL AND/OR AMMONIA PLANTS

[75] Inventors: Hartmut Ilgner; Peter Kledewski, both of Dortmund; Reinhard Heun, Herdecke, all of Fed. Rep. of Germany

[73] Assignee: Uhde GmbH, Dortmund, Fed. Rep. of Germany

[21] Appl. No.: 537,636

[22] Filed: Sep. 30, 1983

[30] Foreign Application Priority Data

Oct. 1, 1982 [DE] Fed. Rep. of Germany ....... 3236441

[51] Int. Cl.³ ............................................... B01F 3/04
[52] U.S. Cl. ................................. 261/128; 261/36 R; 261/151
[58] Field of Search .................... 261/151, 36 R, 117, 261/113, 127–130

[56] References Cited

U.S. PATENT DOCUMENTS

| | | | |
|---|---|---|---|
| 476,274 | 6/1892 | Huck | 261/151 X |
| 1,986,529 | 1/1935 | Ray | 261/128 X |
| 2,220,219 | 11/1940 | Crawford | 261/151 X |
| 2,826,397 | 3/1958 | Lofgren et al. | 261/128 |
| 3,249,152 | 5/1966 | Buss et al. | 261/151 X |
| 3,532,595 | 10/1970 | Arnesjo et al. | 261/128 X |
| 4,276,243 | 6/1981 | Partus | 261/128 |

Primary Examiner—Richard L. Chiesa
Attorney, Agent, or Firm—Toren, McGeady, Stanger, Goldberg & Kiel

[57] ABSTRACT

A process for humidifying a gas stream in a humidifier chamber by passing heated water downwardly through the humidifier and passing gas upwardly through the chamber to transfer water vapor to the gas stream. One or more portions of the water is removed at an intermediate stage in the chamber and the remaining portion of the water collected at the bottom is removed. The intermediate portion and final portion may have make-up water added thereto and the portions are reheated either separately or as a combined mixture. The process provides an improved economic method for humidification with good energy savings.

15 Claims, 3 Drawing Figures

PROCESS FOR HUMIDIFYING A GAS STREAM, PARTICULARLY IN METHANOL AND/OR AMMONIA PLANTS

BACKGROUND OF THE INVENTION

1. Field of the Invention

The invention relates to a process for humidifying a gas stream by passing heated water through a gas humidifier in countercurrent to the gas for the purpose of transferring water vapor to said gas. After the addition of an amount of make-up water corresponding to the amount of water vapor transferred, the water is fed to a heating section and recycled to the gas humidifier.

2. Description of the Prior Art

A process of the above type is known, for example, in the processing of natural gas. In catalytic processes of this kind, a certain water vapor/gas ratio is sometimes necessary and this is achieved with the present state of technology by a process of the type described above. However, the amount of water vapor absorbed is not sufficient and therefore, high temperature, high-grade steam has to be admixed to the gas stream after the latter has left the gas humidifier.

SUMMARY OF THE INVENTION

We have discovered a method for humidifying gas to a particularly high degree and which comes as close as possible to the subsequent operating requirements but, at the same time, permits the use of energy of an inferior quality, in particular, energy at a low temperature level.

More particularly, the present invention comprises humidifying a gas stream by passing heated water through a gas humidifier in countercurrent to the gas for the purpose of transferring water vapor to said gas. During this process, partial streams of the circulating water are withdrawn from the humidifier in several consecutive stages and heated separately and/or jointly.

As a result of the invention, it is no longer necessary to heat the entire water stream from the low temperature at which it leaves the gas humidifier to the higher inlet temperature. Rather, the individual partial streams can be heated in stages.

DESCRIPTION OF THE PREFERRED EMBODIMENT

One embodiment of the present process provides for the circulating water to be withdrawn from the gas humidifier in two stages, the first partial stream being larger than the second partial stream. In principle, other proportions, for instance, two equal partial streams could be used but the division into partial streams as provided by the invention is particularly suitable.

It is an advantage if, as is also provided for in the invention, the second partial stream is passed through a pre-heating stage and then fed to a final heating stage together with the first partial stream. This procedure permits the appropriate pre-heating and final heating stages to be designed within favorable temperature ranges so that even slight differences in temperature are sufficient to heat the water.

According to a further embodiment of the invention, the make-up water is admixed upstream of the first preheating stage to the last partial stream taken from the gas humidifier.

In order to utilize waste heat, e.g., the heat of the synthesis gas from a methanol reactor, in an optimum way for heating the circulating water, the invention provides for the preheating stage or stages and the final heating stage to be connected in series in a common heat stream as heat exchangers for hot synthesis gas. A further embodiment provides for the partial stream from the preceding heat exchanger, which is situated downstream as regards the heat flow, to be fed to the next upstream heat exchanger together with a partial stream from the gas humidifier.

These embodiments of the process configuration according to the invention are particularly expedient because the heat exchangers exposed to the heat flow can be designed in a very favorable way so that, for example, the remaining water from the sump of the gas humidifier is fed to that heat exchanger which is situated furthest downstream, i.e., the coldest heat exchanger, for initial preheating. Then the partial stream of water to be heated from the gas humidifier is taken from the second last point and fed to the next heat exchanger together with the remaining stream which had been subjected to initial preheating. It is advisable to design the facility such that in each case, the partial stream taken from one stage of the gas humidifier is in the same temperature range as the partial stream leaving the preceding preheater which is admixed to this partial stream.

Figure 1:
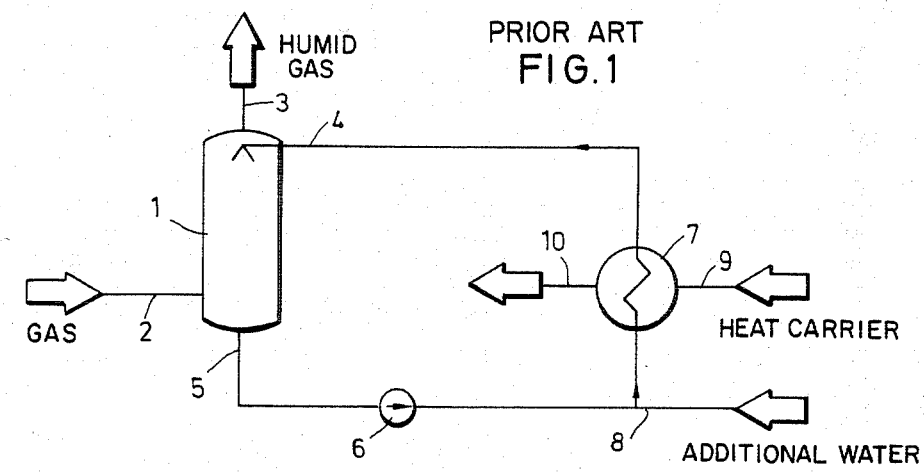
FIG. 1 is a schematic diagram of a process according to the present state of technology.

Referring to FIG. 1, which represents the state of technology on which the present invention is based, the gas to be provided with water vapor is fed via 2 into the lower zone of gas humidifier 1. The gas enriched with water vapor leaves the gas humidifier at the top via 3. Heated water is admitted to the top of the gas humidifier 1 at 4 and withdrawn at the bottom of the sump 5, the amount of injected hot water being higher than the amount withdrawn from the sump by the amount of water vapor with which the gas is enriched. The water which is cooled in the countercurrent and collected in sump 5, is fed to heat exchanger 7 via pump 6, an amount of make-up water which corresponds to the amount of water vapor absorbed by the gas being added to the cycle upstream of heat exchanger 7 at 8. From heat exchanger 7, the heated water is again injected into gas humidifier 1 at 4. Heat exchanger 7 is heated by a hot stream, e.g., hot synthesis gas from a methanol reactor, as indicated by feed line 9 to the heat exchanger and discharge line 10 with the appropriate arrows.

Figure 2:
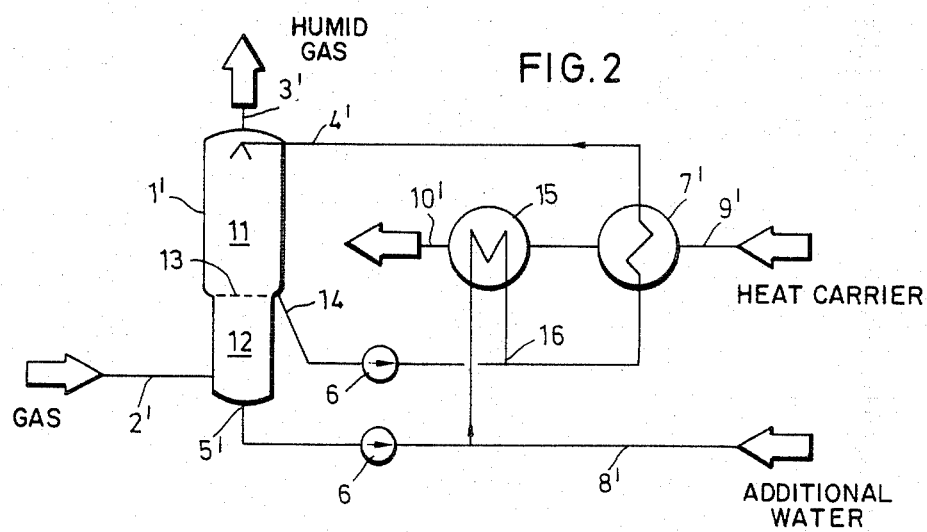
FIG. 2 is a schematic diagram of a process in accordance with the present invention.
Figure 3:
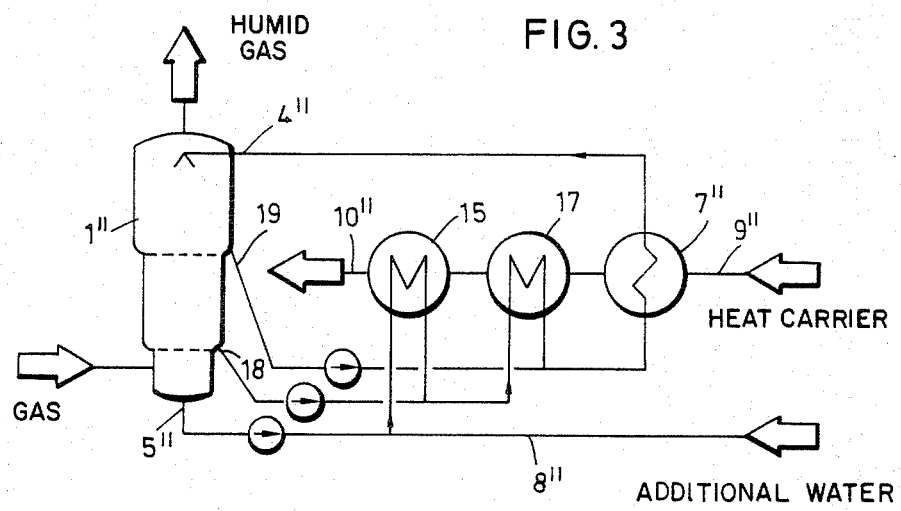
FIG. 3 is a schematic diagram of yet another embodiment of the present invention.

In the description of the invention according to FIGS. 2 and 3, those items of equipment which are basically the same are designated by the same reference numbers, but for easier identification, the numbers are marked with one or two apostrophes. For example, the gas humidifier in FIG. 2 is designated 1' and the gas humidifier in FIG. 3 is designated 1".

The configuration illustrated in FIG. 2 shows a gas humidifier which is basically divided into two zones, an upper zone 11 and a lower zone 12. In the upper zone 11, the total amount of process water is injected at 4' and admixed to the gas which enters the gas humidifier 2' at the bottom and leaves at 3' at the top laden with water vapor.

The broken line 13 in gas humidifier 1' represents the zone division between 11 and 12. At this point, a partial stream of the process water is removed at 14. The residual amount enters the lower zone 12 of gas humidifier 1' and leaves at the sump 5'. The first partial stream which is withdrawn at 14, has a higher temperature than the second partial stream or residual amount. The first partial stream should be larger in the configuration quoted as an example; this is indicated by the different proportions of zones 11 and 12 in gas humidifier 1'.

The first partial stream leaving gas humidifier 1' at 14 is fed by means of pump 6 to heat exchanger 7' which is heated by a heat stream, e.g., synthesis gas from a methanol reactor, as indicated by arrow 9'.

The second partial stream leaving the sump is pumped to a second heat exchanger 15 which is arranged in the heat stream 9'-10' on the colder side, i.e., downstream, as can be seen in FIG. 2. As a result, this partial stream or residual stream is heated to such an extent that it has roughly the same temperature as the first partial stream leaving the gas humidifier at 14. The two partial streams are then united at 16 and fed to the last heat exchanger 7' in this cycle.

FIG. 2 also shows that the make-up water is admixed to the second partial stream or residual stream via 8' and thus subjected to the first preheating step in heat exchanger 15.

FIG. 3 shows another embodiment of the invention wherein along with the final heating stage provided by heat exchanger 7", another heat exchanger 17 is installed in addition to heat exchanger 15 in the same heat stream 9"-10". The routes of the partial streams are basically the same here as in FIG. 2, i.e., make-up water is admixed at 8" to the coldest partial stream or residual stream from sump 5" and passed through the first preheater 15 and then, together with a partial stream leaving the gas humidifier at 18, fed to another heat exchanger 17, where it is further preheated. Together with the first partial stream leaving the gas humidifier 1" at 19, the total amount of water is supplied to the final heating stage, i.e., heat exchanger 7".

It goes without saying that the configurations described here can be modified in a number of ways without abandoning the fundamental idea of the invention. The invention is therefore not restricted to any special design of the items of equipment used in the process, nor to the process configuration illustrated in the diagrams. With regard to design, equipment can also be arranged in parallel instead of in series, to name but one possibility.

We claim:

1. A process for humidifying a gas stream comprising passing heated liquid water through a gas humidifier chamber countercurrently to the flow of the gas stream to transfer water vapor to the gas stream, removing one or more portions of the liquid water at an intermediate stage during the water's passage through the chamber, removing the remaining portion of liquid water from the chamber, adding make-up water to the removed water corresponding to the amount of water vapor transferred, heating all the water portions and recycling them to the humidifier chamber.

2. The process of claim 1 wherein more than one intermediate portion of water is removed from the chamber sequentially and each portion is larger than the portion following it.

3. The process of claim 2 wherein there are two intermediate portions.

4. The process of claim 2 wherein the remaining portion and each intermediate portion except the first such portion are passed through separate preheating stages and are then combined with the first portion and the combined portions are passed through a first heating stage prior to recycling to the humidifier chamber.

5. The process of claim 4 wherein there are two intermediate portions.

6. The process of claim 5 wherein the make-up water is added to the remaining portion prior to the preheating stage.

7. The process of claim 4 wherein the make-up water is added to the remaining portion prior to the preheating stage.

8. The process of claim 7 wherein the make-up water is added to the remaining portion prior to the preheating stage.

9. The process of claim 4 wherein the preheating stage and first heating stage are each a separate heat exchanger connected in series and have a common heat supply stream which enters the series at the first heat exchanger and then proceeds to and through the next heat exchanger in the series and wherein each removed portion passes through the respective heat exchanger corresponding to the order of removal of the portion from the humidifier.

10. The process of claim 9 wherein there are two intermediate stages and two corresponding heat exchangers in addition to the first heat exchanger.

11. The process of claim 9 wherein the final and each intermediate portion after exiting its respective preheating stage is combined with the next earlier removed portion prior to said earlier portions entering its respective heating stage.

12. The process of claim 1 wherein one intermediate portion is removed from the chamber which portion is larger than the remaining portion.

13. The process of claim 12 wherein the remaining portion is passed through a preheating stage and is then combined with the intermediate portion and the combined portions are passed through a first heating stage prior to recycle to the chamber.

14. The process of claim 13 wherein the make-up water is added to the remaining portion prior to the preheating stage.

15. The process of claim 13 wherein the preheating stage and first heating stage are each a separate heat exchanger connected in series and have a common heat supply stream which enters the series at the first heat exchanger and then proceeds to and through the preheating stage heat exchanger.

* * * * *